US005713841A

United States Patent [19]

Graham

[11] Patent Number: 5,713,841

[45] Date of Patent: Feb. 3, 1998

[54] INFLATABLE CERVICAL CERVICO-THORACIC THORACO-LUMBAR AND LUMBAR EXERCISING DEVICE

[76] Inventor: Richard A. Graham, 18582 Main St., Huntington Beach, Calif. 92648

[21] Appl. No.: 681,889

[22] Filed: Jul. 29, 1996

Related U.S. Application Data

[63] Continuation-in-part of Ser. No. 351,787, Dec. 9, 1994, Pat. No. 5,569,176, which is a continuation of Ser. No. 17,042, Feb. 12, 1993, Pat. No. 5,382,226.

[51] Int. Cl.[6] .......... A61F 5/00

[52] U.S. Cl. .......... 602/32; 606/240; 128/DIG. 20; 5/636; 602/36

[58] Field of Search .......... 602/32, 33, 34, 602/35, 36, 18, 19, 38, 60, 61; 601/23, 148, 149, 151, 152; 5/636; 606/240, 241; 128/DIG. 20

[56] References Cited

U.S. PATENT DOCUMENTS

| | | | |
|---|---|---|---|
| Re. 32,791 | 11/1988 | Saunders | 602/32 |
| 4,114,611 | 9/1978 | Lyle et al. | 602/32 |
| 4,583,255 | 4/1986 | Mogaki et al. | 601/150 |
| 4,669,455 | 6/1987 | Bellati | 606/240 |
| 4,981,131 | 1/1991 | Hazard | 128/69 |
| 5,181,904 | 1/1993 | Cook et al. | 602/32 |
| 5,279,310 | 1/1994 | Hsien | 602/32 |
| 5,338,276 | 8/1994 | Jull et al. | 601/23 |
| 5,382,226 | 1/1995 | Graham | 602/32 |
| 5,410,472 | 4/1995 | Anderson | 364/413.04 |

FOREIGN PATENT DOCUMENTS

| | | | |
|---|---|---|---|
| 2638077 | 3/1977 | Germany | 602/32 |
| 404327849 | 11/1992 | Japan | 601/148 |
| 8700424 | 1/1987 | WIPO | 602/32 |

*Primary Examiner*—Robert A. Hafer
*Assistant Examiner*—Justine R. Yu
*Attorney, Agent, or Firm*—Walter A. Hackler

[57] ABSTRACT

A spinal traction and exercise device adapted to be secured about the spine for imparting the desired lordotic shape into the cervical, cervico-thoracic, thoraco-lumbar, and lumbar regions of the spine and manipulating the spine and surrounding tissue to promote fluid and cellular exchange in and around the intervertebral discs. The device includes a cervical unit and a thoraco-lumbar unit and is designed so each unit can work independent of each other or in conjunction with each other. The device includes a frame, upstanding neck and back supports carried by the frame inflatable bladders carried by the neck and back supports, restraining arms or straps for securing the device to the user's body such that the bladders are disposed below and adjacent the user's spine, and means for selectively inflating and deflating the bladders to force the cervical, cervico-thoracic, thoraco-lumbar and lumbar spine to curve forwardly and apply angular/circular traction to the spine. The method of the present invention results from operation of the device.

12 Claims, 5 Drawing Sheets

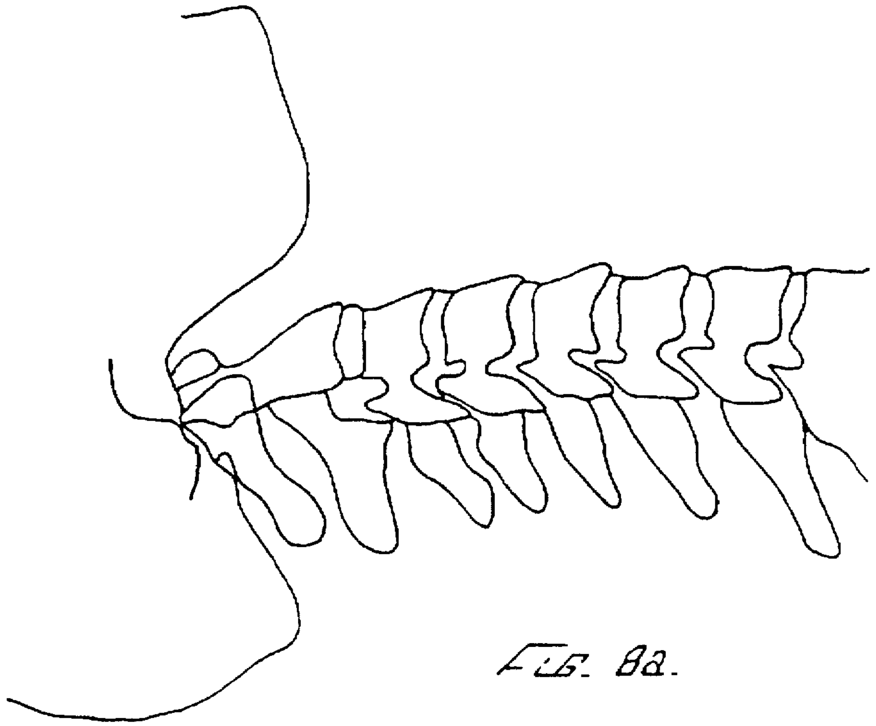
FIG. 8a.
FIG. 8b.
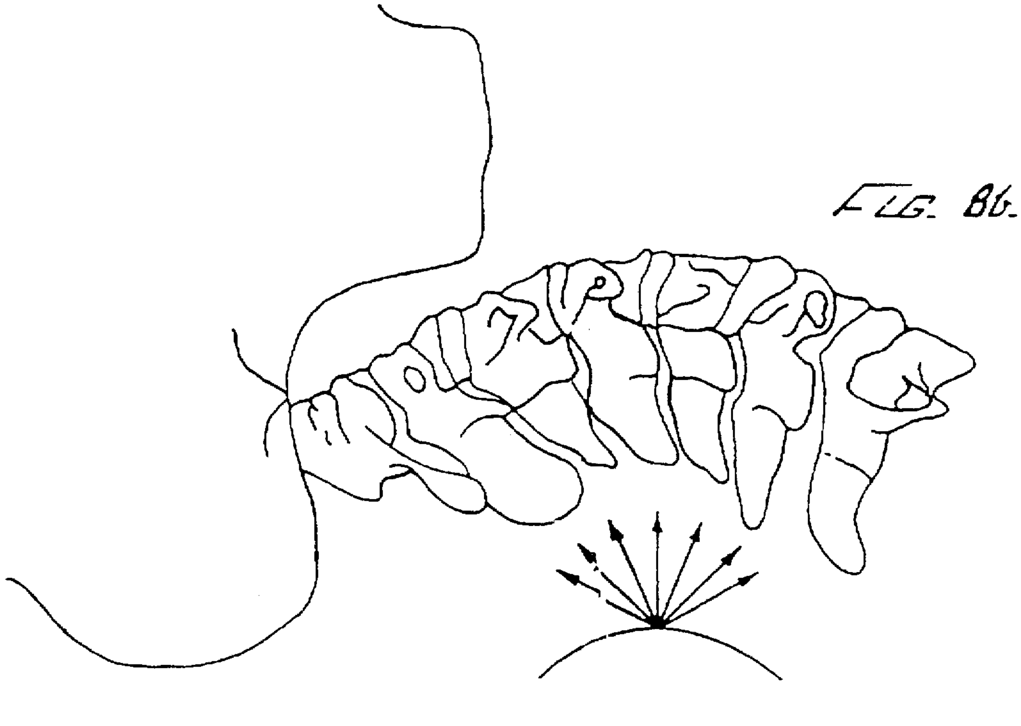

INFLATABLE CERVICAL CERVICO-THORACIC THORACO-LUMBAR AND LUMBAR EXERCISING DEVICE

This application is a continuation-in-part of U.S. Ser. No. 08/351,787, filed Dec. 9, 1994, now U.S. Pat. No. 5,569,176, which is a continuation of U.S. Ser. No. 08/017,042, filed Feb. 12, 1993, now U.S. Pat. No. 5,382,226.

BACKGROUND OF THE INVENTION

The present invention relates to a spinal traction and exercising device and method for restoring natural shape while stimulating and promoting fluid imbibition in the spine. The lumbar and cervical regions of the spine normally define forward curves of about 35 to 45 degrees whereby weight is distributed relatively evenly on the individual articular surfaces and discs. Research has shown that without these forward curves in the cervical and lumbar spinal regions, the weight of the body bears forwardly on the soft non-bony intervertebral discs causing the discs to wear and degenerate. Additionally, individuals with diminished, lost or reversed cervical and lumbar spinal curves exhibit a significant loss of the natural joint movement, limiting the normal canaliculus seepage and imbibition of adjacent fluids via vertebral end plates and annuli. Without such nutrient rich fluids, the discs tend to dehydrate, further weakening the discs, resulting in a further loss of mobility, degeneration and possibly nerve damage. Active nutrient transport is particularly important because the intervertebral discs' indigenous vascular supply disappears at approximately 20 years of age.

Spinal traction devices have heretofore been developed for the purpose of restoring the normal lordotic curve in the cervical area of the spine to prevent disc generation. Such devices have typically comprised a flat U-shaped support frame having a V-shaped neck support projecting outwardly from the lower portion of the frame. One or more straps were secured to the frame which extended about the wearer's forehead and/or under jaw to secure the traction device to the user's head. Upon positioning the neck support under a stress point in the cervical area of the spine and tightening the straps about the user's forehead and/or jaw, the head is pulled rearwardly about the neck support as the neck support bears against the neck, forcing the cervical area of the spine into a lordotic shape. Repeated periodic use of the user's neck, the extent to which the neck support projects above the horizontal surface on which the user and traction device are disposed, and the rearward force exerted on the head by the restraining straps. As the shape and size of the user's neck and the outward extension of the neck support are fixed, the only adjustments which can be made in the force exerted on the cervical spine with such devices is in the tightening of the restraining straps. Those straps, however, cannot be readily tightened without first being loosened and relieving the pressure on the spine, nor are they well adapted for providing a controlled traction against the spine. As a result, the force exerted on the spine is neither continuously nor incrementally variable with any degree of precision. Thus, a user could not gradually increase the magnitude of the spinal arc to his or her level of tolerance with such devices without having to intermittently relieve the pressure on the spine. If the user were capable of such control, the efficiency of the device in imparting curvature into the spine would be greatly enhanced. In addition, these devices while arching the spine do not adequately work the spine and surrounding tissue which., if done, would actively promote fluid imbibition in the discs and thereby further enhance the rehabilitation process. The cervical traction and exercising device of the present invention overcomes these shortcomings in the prior art.

SUMMARY OF THE INVENTION

In general, the present invention relates to a traction and exercising device and method for imparting the desired lordotic shape into the cervical, cervico-thoracic, thoraco-lumbar, and lumbar regions of the spine and working the spine and surrounding tissue to promote fluid and cellular exchange in and around the intervertebral discs. More particularly, the device, in accordance with the present invention, may include frames, substantially ellipsoidal inflatable bladders transversely in neck and back support cradles carried by the frames, and restraining arms or straps for securing the device to the user's head and body such that the bladders are disposed against the back of the neck and thoraco-lumbar spine under stress points in the spine.

Inflation of the bladders by the user is controlled by means of a hand-held or electronic pump and/or blower, which causes a controlled lifting and a stretching of the cervical, cervico-thoracic, thoraco-lumbar, and lumbar spine. As the bladders are inflated, the configuration of the bladders cause the bladders to expand vertically and to a lesser extent, transversely. The vertical expansion lifts the spine, creating a spinal apex while the transverse expansion applies an angular or circular traction to the spine on both sides of the apex. By controlling the inflation of the bladder, the user can control the lifting and stretching of the spine and incrementally increase the magnitude of spinal arc to his or her own tolerance. As the bladders are repetitively inflated and deflated, the spine is alternatively and actively forced from a lesser arc to a greater or hyperlordotic arc, thereby promoting nutrient transport to the intervertebral disc while simultaneously increasing the lordotic arc. In the place of air, liquid can be used to inflate the bladders. Heating or cooling the liquid can have significant therapeutic affects. For example, cold tends to promote vasoconstriction, reducing swelling, while heat brings fluid to the area enhancing fluid exchange.

In accordance with one embodiment of the present invention, the traction and exercise device in accordance with the present invention for imparting a forward curve to the cervical and lumbar regions of the spine and additionally for promoting fluid imbibition in the cervical and lumbar regions of the spine, generally includes a frame and a head support disposed in the frame and including a neck support.

Means are provided for securing the head support to a user's head such that the neck support is positioned transversely across a back of the user's neck. A first means is provided for applying force against the back of a user's neck, with the force both lifting and stretching the cervical spine away from the neck support such that a lordotic arc is exercised in the cervical spine.

A transverse lumbar support is disposed on the frame in a spaced-apart relationship with a head support and a second means for applying a force against the user's lumbar regions provided for both lifting and stretching the lumbar spine away from the lumbar support such that the lordotic arc is exercised in the lumbar spine.

Means are provided for adjusting the spaced-apart relationship between the head support and the transverse lumbar support and, further, means for enabling the user to simultaneously and alternatively control the first and second means in order to increase and/or create the lordotic arc in the cervical and lumbar spine and to promote fluid imbibition in the cervical and lumbar spine regions.

A method in accordance with an embodiment of the present invention generally includes providing a support frame as well as a neck support carried by the frame.

A lumbar support is provided and carried by the frame.

Further, the method includes positioning the neck support transversely across the back of a user's neck and adjusting a distance between the neck support and the lumbar support and positioning the lumbar support frame transversely across a lumbar region of the user's spine.

A bladder is inflated between the user's neck and the neck support in a first direction outwardly from the neck support toward the user's neck, thereby forcing the cervical spine to curve forwardly.

A method further includes a step of inflating a bladder between the user's lumbar region and the lumbar support in a first direction outwardly from the lumbar support toward the user's lumbar region forcing the lumbar spine to curve forwardly.

The bladders are selectively inflated and deflated forcing the cervical and lumbar spine to curve forwardly and repeating inflation and deflation of the bladders in order to transfer fluid to the intervertebral discs.

It is the principal object of the present invention to provide a cervical, cervico-thoracic, thoraco-lumbar, and lumbar traction and exercising device for preventing degeneration of the stress areas of the spine. It is another object of the present invention to provide a device for restoring a normal lordotic shape to the cervical, cervico-thoracic, thoraco-lumbar, and lumbar regions of the spine.

It is another object of the present invention to provide a device for exercising the discs and vertebrae in the cervical, cervico-thoracic, thoraco-lumbar, and lumbar regions of the spine to promote normal fluid transport to the intervertebral discs.

It is a further object of the present invention to provide a device for restoring the normal lordotic curve to the cervical, cervico-thoracic, thoraco-lumbar, and lumbar regions of the spine which allows the user to readily regulate the lifting and stretching motion of the device to his or her own tolerance.

It is a still further object of the present invention to provide a user controlled cervical and lumbar traction device for concurrently forcing the cervical, cervico-thoracic, thoraco-lumbar, and lumbar spine forwardly and stretching the spine angularly or circularly to restore the spine to its normal lordotic shape and/or exercise the spine to promote fluid transfer in and around intervertebral discs.

BRIEF DESCRIPTION OF THE DRAWINGS

The advantages and features of the present invention will be better understood by the following description when considered in conjunction with the accompanying drawings in which:

FIGS. 8(*a*) and 8(*b*) are schematic representations illustrating the operation of the device on the cervical spine;

DETAILED DESCRIPTION

Figure 1:
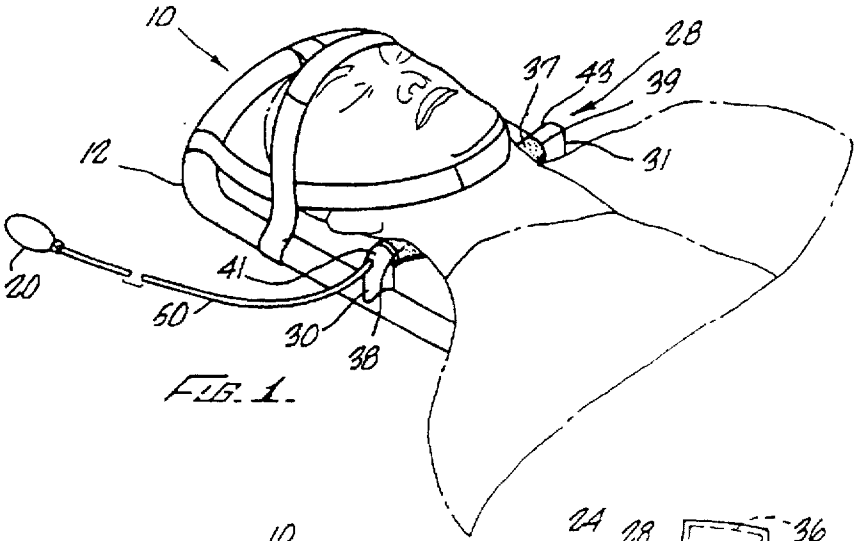
FIG. 1 is a perspective view of the traction and exercising device of the present invention.
Figure 2:
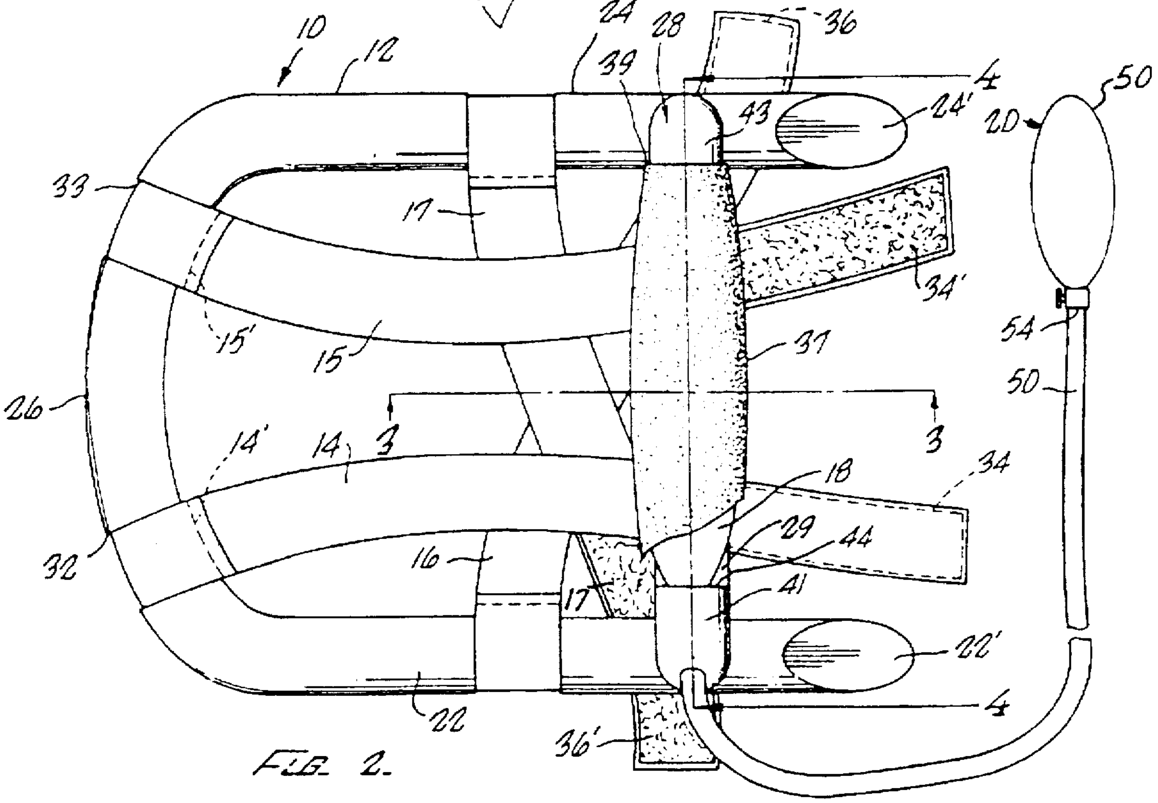
FIG. 2 is a plan of the device of the present invention.

Referring now to FIG. 1, a cervical traction and exercise device 10 in accordance with one embodiment of the present invention Comprises a frame 12, a pair of chin restraint straps 14 and 15, a pair of forehead restraint straps 16 and 17, an inflatable air bladder 18 and an air pump assembly 20. The frame 12 is preferably molded of a durable plastic material in a tubular configuration so as to define a pair of side members 22 and 24, an arcuate spanning member 26 and a transverse neck support 28. The frame side members 22 and 24 are preferably slightly bowed and terminate in tapered ends 22' and 24'. The neck support 28 includes vertically extending portions 30 and 31 which project outwardly from the side members 22 and 24 respectively and project inwardly at 30' and 31' to define inwardly directed raised lateral portions 41 and 43. A neck cradle 29 extends transversely between portions 41 and 43, spanning frame side members 22 and 24.

The chin restraint straps 14 and 15 are each secured at an end thereof to opposed inclined lateral portions 32 and 33 of spanning member 26 so as to angularly extend therefrom such that the straps can be readily passed in an arcuate path under the user's chin and be secured together by interlocking hook and loop fasteners 34 and 34' disposed adjacent the extended ends of the straps. To secure the restraining straps 14 and 15 to the inclined portions 32 and 33 of the frame, portions 32 and 33 are preferably formed of a reduced diameter such that the ends of the straps can be looped thereover and sown against themselves at 14' and 15'. The forehead restraining straps 16 and 17 are each similarly secured at one end thereof to the frame side members 22 and 24 respectively and are spaced from the transverse neck support 28 such that straps 16 and 17 can be readily passed in an arcuate path over the user's forehead and secured together by interlocking hook and loop fasteners 36 and 36' disposed adjacent the extended ends of the straps. By such a strap configuration, the cervical traction and exercise device 10 can be easily and securely affixed to the user's head such that with the user lying flat on his or her back on a horizontal surface, the frame 12 rests on the surface and the neck support 28 is disposed under the user's neck and the tapered ends 22' and 24' of the frame side members are substantially adjacent the user's shoulders. The tightness of the securement of the device 10 to the user's head can be readily adjusted as needed by means of the hook and loop fasteners on the securement straps 14–17.

Figure 4:
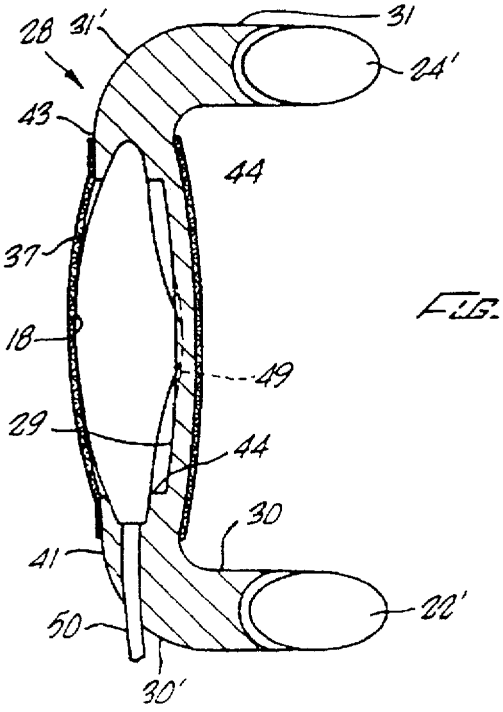
FIG. 4 is a section view taken along the line 4—4 in FIG. 1.

As seen in FIGS. 1 and 4, the expandable bladder 18 is carried by the neck support 28 in the cradle 29 defined therein and is preferably secured in place by an open ended elastic sleeve 37 which is disposed about the bladder 18 and cradle 29. Sleeve 37 is held in place by an elastic fitment of the open ends 38 and 39 of the sleeve disposed about the raised lateral portions 41 and 43 of neck support 28. The lateral portions 41 and 43 of neck support 28 are preferably provided with oppositely facing recesses 44 formed therein adjacent the lateral ends of cradle 29 for receiving the extended ends 18' of bladder 18 to facilitate retention and alignment of the bladder on the cradle 29.

Figure 3:
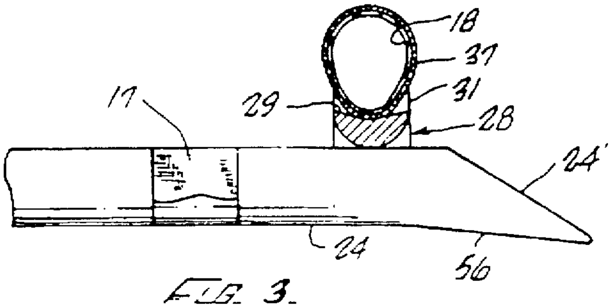
FIG. 3 is a section view taken along the line 3—3 in FIG. 1.
Figure 5:
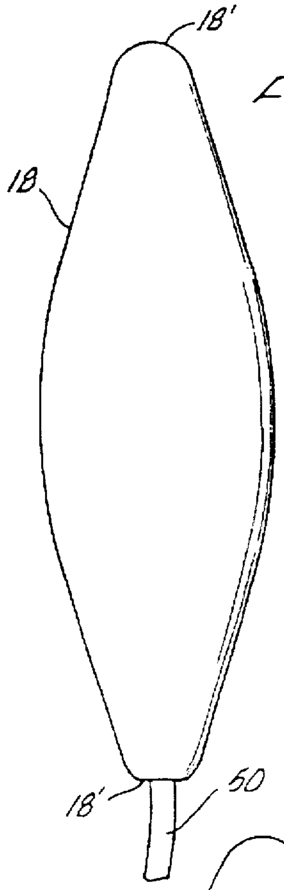
FIG. 5 is a top plan view of the bladder employed in the present invention illustrated in a fully inflated position.
Figure 6:
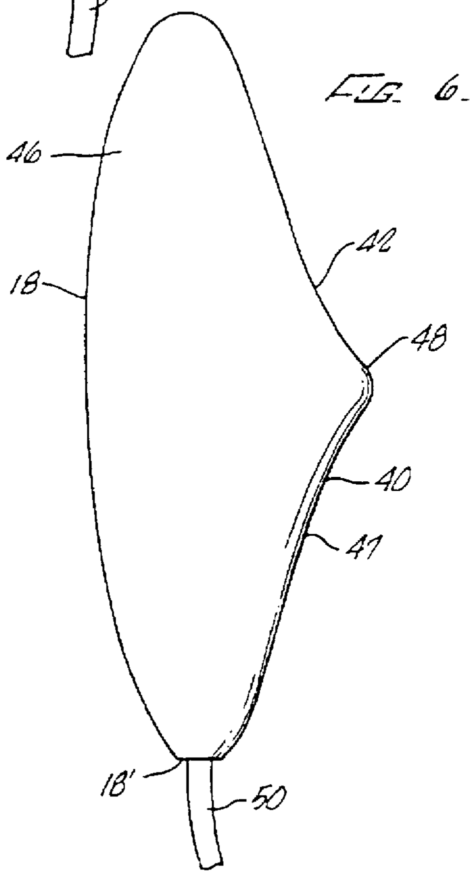
FIG. 6 is a side view of the bladder employed in the present invention, illustrated in a fully inflated state.

As seen in FIGS. 5 and 6, the upper portion 46 of bladder 18 is of a generally semi-ellipsoidal configuration having relatively pointed ends 18' similar to the upper half of a football bladder. In the preferred bladder configuration, the underside 47 of bladder 18 is formed with undercut portions at 40 and 42 so as to define a central depending portion 48 as seen in FIG. 3.

A shallow trough 49 is preferably formed in cradle 29 to receive the underside of bladder 18. As a result of this bladder configuration, bladder 18, when inflated, will expand upwardly from the cradle 29 to a slightly greater extent than in a transverse direction. Additionally, it has been found that the provision of the depending portion 44 on the underside of the bladder provides a cushioning effect under the apex of the expanded bladder which bears against the user's neck, making the device more comfortable for the user. Thus, as the bladder is inflated under and against the user's neck, it expands vertically and transversely, lifting the spine to create a spinal apex and applying an angular traction to the neck on both sides of the spinal apex. The amount of traction exerted in the vertical direction, however, will be somewhat greater than that exerted longitudinally to obtain the vertical lift necessary to restore the normal lordotic shape to the cervical region of the spine without overly tractioning the neck longitudinally.

Figure 7:
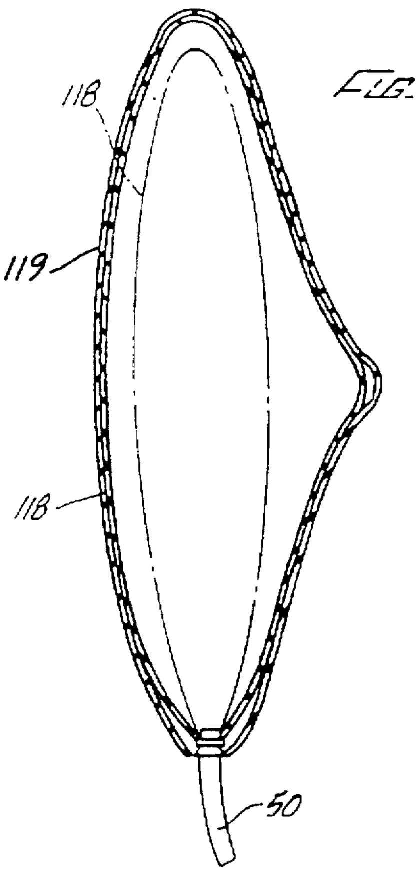
FIG. 7 is a sectional side view illustrating an alternate embodiment of the bladder.
Figure 9:
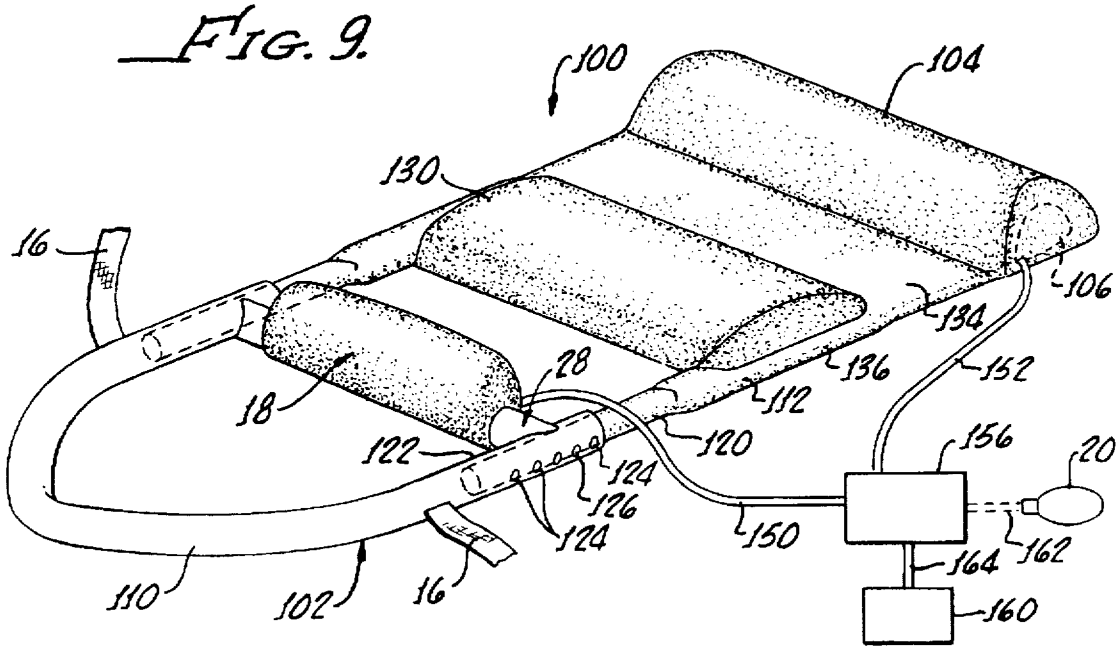
FIG. 9 is a perspective view of another embodiment of the present invention.

In an alternate embodiment of the invention, illustrated in FIG. 7, the expandable bladder 118 is of a tubular configuration (illustrated in phantom lines) and is disposed in a non-expandable casing 119, preferably constructed of a vinyl material. Casing 119 is preferably formed in the above described generally ellipsoidal configuration of bladder 18. As the tubular bladder expands upon inflation, the expansion is limited by the configuration of the casing 120 to provide the desired increase in the vertical direction relative to the transverse direction as seen in FIG. 7. While the above described bladder configurations are preferred, it is to be understood that other configurations of expandable bladders could be employed in the present invention, either with or without an expansion controlling casing to provide the desired lifting and traction of the user's neck.

To provide selective inflation and deflation of the of the bladder, a flexible air line 50 communicates the interior of bladder with a conventional hand operated air pump 20. A conventional pressure relief valve 54 is disposed between the air line 50 and pump 52. Air line 50 preferably extends from the relief valve 54 through an opening in the neck support 28 and communicates with the bladder 18 through an opening formed in either the underside or, as shown in the drawings, through one end of the bladder.

In use, the traction and exercising device 10 rests on a horizontal surface such that the neck support 28 projects upwardly therefrom. The user lies on the device in a prone position such that the back of the neck rests on the deflated bladder 18 carried in the cradle 29 of the neck support 28. The chin and forehead restraining restraint straps 14–17 are respectively extended under the user's chin and about the user's forehead secured by the hook and loop fasteners 34 and 36, thereby affixing the traction and exercising device 10 to the user such that the neck and cervical spine extend over the neck support and bladder. In the preferred configuration of the invention, the outward extension of the neck support. 28 is relatively slight so that when the bladder is in the deflated position with the forehead and chin restraints secured, very little or no force is exerted on the neck by the neck support. This is achieved by elevating the neck support 28 above the frame such that the neck cradle 29 formed therein is about 2.5–3 inches above the floor or other horizontal surface on which the device 10 is used. The bladder is sized such that upon full inflation, the apex of the curved upper surface of the bladder will extend about 5 inches above the floor.

As the user slowly inflates the bladder 18 by means of any suitable air pump, fluid pump or blower 50, the bladder expands upwardly and, to a lesser extent, transversely, thereby forcing the cervical spine forwardly creating a spinal apex while concurrently stretching the spine angularly along both sides of the formed spinal apex. The user then continues to inflate the bladder until his or her individual tolerance level is reached. The bladder is then deflated by use of the one way valve 52. The process is repeated several times, slowly increasing the spinal arc as the level of tolerance increases. In addition, the bladder can be held in an inflated state at or slightly below the level of tolerance for varying periods of time up to ten to twenty minutes. Through such repetition, the cervical spine and surrounding tissue receive a workout promoting cellular exchange in and around the intervertebral disc and a forward curve is reinstated into the cervical spine. FIGS. **8*a* and 8*b* illustrate the effect of the traction and exercise device 10** of the present invention on the cervical spine.

By way of example, a frame 12 of a traction and exercise device 10 made in accordance with the present invention defines a spacing of about nine inches between the side members 22 and 24 with each side member being of a tubular configuration 1.5 inches in diameter, about 11–12 inches in length, and being bowed slightly at 56 (see FIG. 3) proximate the extended ends 22' and 24' thereof to elevate the underside of the frame side members 22 and 24 disposed beneath the lateral ends of the neck support 28 about 0.5–0.75 inches above the floor. Such a configuration causes the extended ends 22' and 24' of the frame to bear against the floor during use and reduce the tendency of the frame to twist about its transverse axis. The arcuate frame spanning member 26 extends the overall length of the frame to about 15–17 inches. The cradle 29 in neck support 28 tapers from an elevation of about 3 inches above the floor proximate side members 22 and 24 to a central elevation of about 2.5 inches. The bladder 18 is constructed of an expandable material such as neoprene rubber, such as neoprene rubber, defines a length of about 9.25 inches, a height of about 3–4 inches in an uninflated state, depending on, the configuration of the bladder and a transverse width of about 3 inches. The semi-ellipsoidal upper portion of the bladder, when inflated, defines a transverse arc of about 4 inches in length about the center of the bladder. It is to be understood that these dimensions are by way of example only and could be varied, as could the configuration of the frame and bladder without departing from the spirit and scope of the invention.

Another embodiment 100 of the present invention is shown in FIGS. 9–12. It should be appreciated that like reference numerals or characters set forth in FIGS. 9–12 refer to identical or corresponding parts of the embodiment 10 as shown in FIGS. 1–8B.

In addition to a first inflatable bladder 18, there is provided a second inflatable bladder 104 disposed on a transverse lumbar support 106 similar to the neck support 28.

In this embodiment 100, the frame 102 includes an upper portion 110 for supporting the transverse neck support 28 and a lower portion 112 for supporting the transverse lumbar support 106.

In accordance with the present invention, a spaced-apart relationship between the neck support 28 and the lumbar support 106 is adjustable to accommodate for users of different physic. Preferably this means includes a telescoping arrangement between an end 120 of the lower frame and an end 122 of the upper frame 110 as shown most clearly in FIG. 9. A diameter of the end 120 is sized for insertion to the end 122 to provide a frictional engagement to maintain the spaced-apart relationship between the supports 28, 106, or alternatively, a plurality of holes 124 in the frame end 122 are sized for accepting a spring loaded pin head 126 to provide a locking arrangement.

Figure 10:
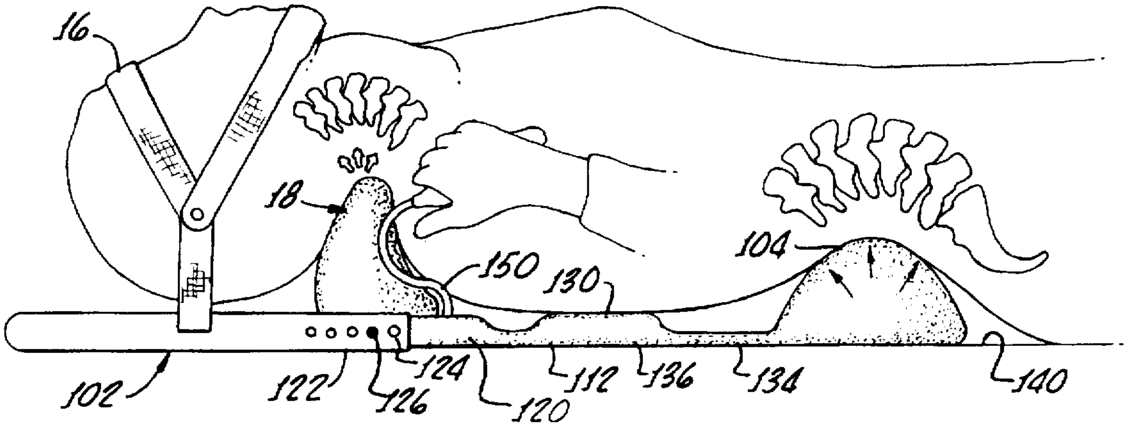
FIG. 10 is a cross-sectional view of the embodiment shown in FIG. 9 demonstrating user on a flat surface with a user in a prone position.
Figure 11:
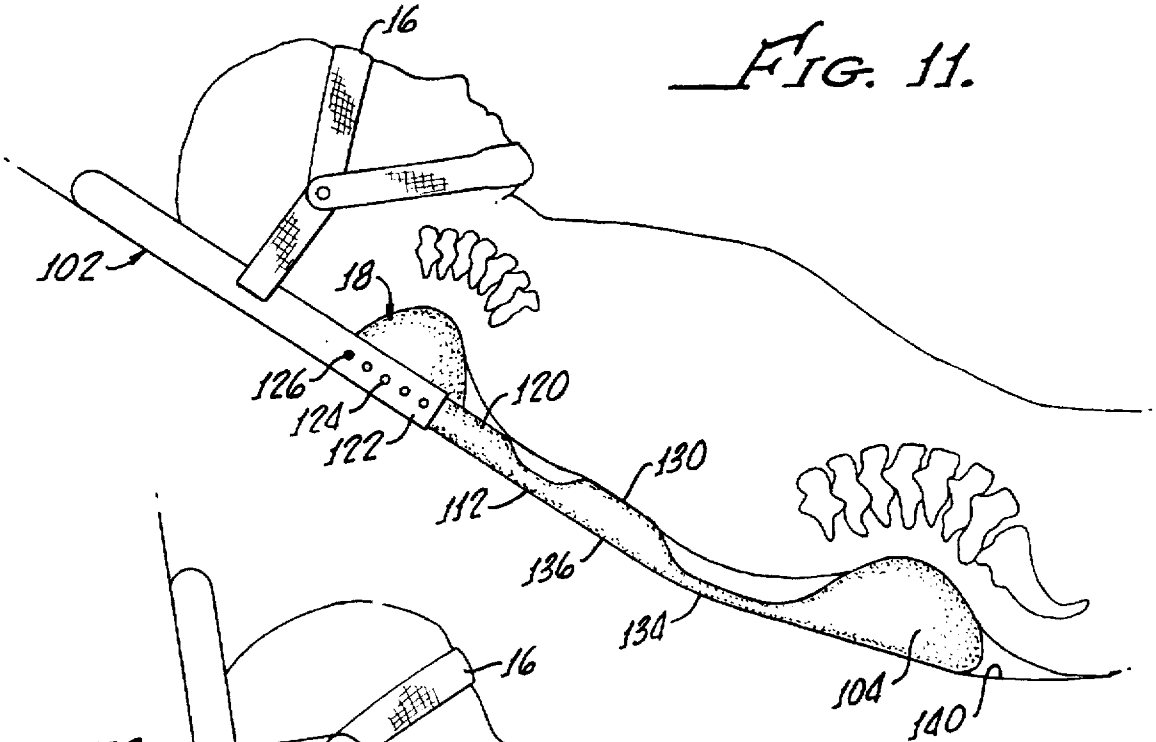
FIG. 11 is a cross-sectional view similar to FIG. 9 showing a user in a reclined position.
Figure 12:
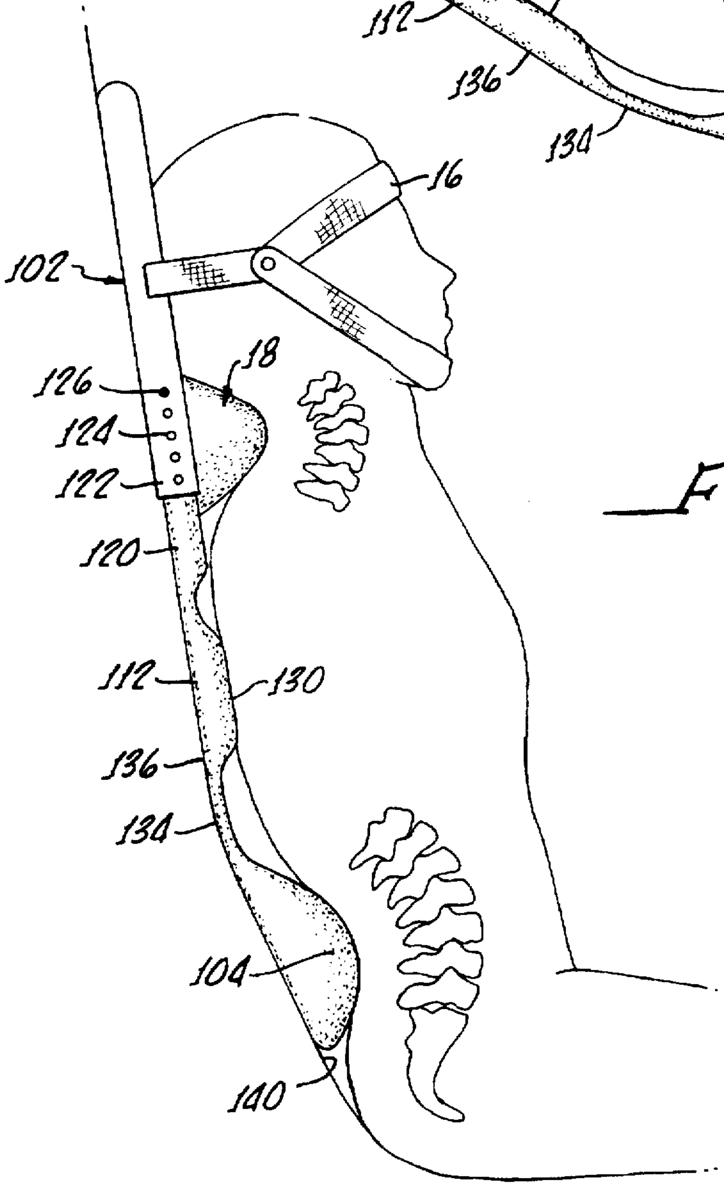
FIG. 12 is a cross-sectional view similar to FIGS. 9 and 10 showing a user in a seated position.

This arrangement provides the advantage for the use of the end device 100 in not only a prone position as shown in FIG. 10, but in a reclining end upright position as shown in FIGS. 11 and 12, respectively. Most particularly, as shown in FIG. 12, when the user's body is exposed against a pad 130, stabilization and a fixed spaced-apart relationship between the supports 28 and 106, and accordingly, the inflatable bladders 18, 104 are properly positioned against the user's body. Thus, this embodiment 100 enables the use of the device in a sitting position without slippage of the bladders 18, 104.

It should be appreciated that the construction of the bladder 104 may be identical to that of the bladder 18 as hereinbefore described.

The construction of the frame 102 may be similar to that hereinbefore described in connection with the frame 12 and the pad or cushion, 130, may be constructed from any suitable material for providing of a padded engagement with the user's body. The lower frame 112 may include a relatively flat flexible portion 134 interconnecting the transverse lumbar support 106 with the frame portion 136 supporting the pad 130. This provides a means for enabling angular movement between the head support of 28 and the transverse lumbar support 106. This arrangement further accommodates the multiple use of the device 100 on a flat surface 140 shown in FIG. 10 and inclined surface 142 shown in FIG. 11 in a relatively vertical surface 144 shown in FIG. 12. This angular motion accommodates for body position and ensures proper contact of the bladders 18, 104 with the respective cervical and lumbar portions of the user's body. Air lines 150, 152 interconnect the bladders 18, 104 respectively, with a control valve 156 which provides a means for enabling a user to simultaneously and alternatively control the first and second bladder means 18, 104, in order to increase the lordotic arc in the cervical and lumbar spine and to promote fluid imbibition in the cervical and lumbar regions.

Air may be supplied to the control valve 156 by a manual air pump assembly 20 as hereinbefore described or an electrical air pump or blower 160, each shown interconnected with the control valve 156 by lines 162, 164, respectively.

It should be appreciated that the control valve 156 may be a simple manually settable valve to control the relative amounts of pressure provided to the bladders 18, 104 by the air pump 20, 160, or alternatively may include a programmable electronic component, not shown, for enabling a programmed inflation and deflation of the bladders 18, 104, respectively, such inflation and deflation being in concert or independently or sequentially coordinated as may be prescribed by an attending health care professional or a user.

Although there has been hereinabove described a specific arrangement of an inflatable cervical, cervico-thoracic, thoraco-lumbar, and lumbar exercising device in accordance with the present invention with the purpose of illustrating the manner in which the invention may be used to advantage, it should be appreciated that the invention is not limited thereto. Accordingly, any and all modifications, variations or equivalent arrangements which may occur to those skilled in the art, should be considered to be within the scope of the present invention as defined in the appended claims.

What is claimed is:

1. A traction and exercising device for imparting a forward curve to the cervical and lumbar regions of a spine and manipulating the spine and intervertebral discs to promote fluid transfer to the discs, said device comprising:
   - a support frame;
   - a transverse neck support carried by said frame and projecting upwardly therefrom;
   - a neck cradle defined by said transverse neck support;
   - a first inflatable bladder carried by said neck support within said cradle, the first bladder defining an upper portion and a lower portion, said lower portion being disposed within said cradle and defining a centrally disposed depending portion, and a pair of undercut portions adjacent said depending portion, said depending portion being disposed in said cradle and, upon inflation of the first bladder, said depending and undercut portions causing the first bladder to expand in a first direction outwardly from said neck support and in a second direction transverse to the first direction, said expansion in the first direction being a distance greater than the expansion of the first bladder in the second direction and said upper portion of the first bladder defining a substantially semi-ellipsoidal configuration;
   - means for securing the first bladder within said cradle;
   - means, carried by said frame, for securing said device to a user's head in order to cause the neck support to transverse a cervical spine of the user;
   - means for enabling repeated inflation and deflation of the first bladder in order to force the cervical spine to curve forwardly by expansion of the bladder in the first direction and to apply an angular traction to said cervical spine by expansion of the bladder in the second direction such that upon the repeated inflation and deflation of the first bladder, a forward curve is imparted to the cervical spine and fluid transfer to the intervertebral discs is actively induced;
   - a transverse lumbar support carried by said frame and projecting upwardly therefrom;
   - a second inflatable bladder carried by said transverse lumbar support; and
   - means for enabling repeated inflation and deflation of the second bladder in order to force a lumbar spine of the user to curve forwardly.

2. A traction and exercising device for imparting a forward curve to the cervical and lumbar regions of a spine and for promoting fluid imbibition in the cervical and lumbar regions of the spine, said device comprising:
   - a frame;
   - a head support disposed on said frame and having a neck support:
   - means for securing the head support to a user's head in order to position the neck support transversely across a back of the user's neck;
   - first means, disposed on the neck support, for lifting and stretching a cervical spine of the user by applying a force away from the neck support and against the back of the user's neck in order to exercise a lordotic arc in the cervical spine, said first means including means for causing said first means to expand in a first direction outwardly from said neck support and in a second direction transverse to the first direction, the expansion in the first direction being a distance greater than the expansion in the second direction;

a transverse lumbar support disposed on said frame in a spaced apart relationship with said head support;

second means for lifting and stretching a lumbar spine of the user by applying a force away from the transverse lumbar support and against the user's lumbar spine in order to exercise a lordotic arc in the lumbar spine;

means for adjusting the spaced apart relationship between the head support and said transverse lumbar support; and means for enabling the user to simultaneously and alternatively control both the first means and second means in order to increase the lordotic arc in the cervical, cervico-thoracic, thoraco-lumbar and lumbar spine and to promote fluid imbibition in the cervical and lumbar spinal regions.

3. The device according to claim 2 wherein said frame includes means, comprising a flexible portion of said frame, disposed between said head support and said transverse lumbar support, for enabling angular movement between said head support and said transverse lumbar support.

4. The device according to claim 2 wherein said first and second means each comprise an inflatable bladder.

5. The device according to claim 4 wherein the means for enabling the user to simultaneously and alternately control both the first means and the second means comprise both a pump for inflating the bladders and a release valve for deflating the bladders.

6. The device according to claim 2 wherein the means for securing the head support, comprises means, including a chin strap and a forehead strap, for immobilizing the user's head during lifting and stretching of the neck by the first means.

7. The device according to claim 2 wherein said first means and said second means each comprise an expandable, elastic bladder.

8. The device according to claim 2 wherein the frame includes means, comprising a flexible portion of said frame, disposed between said head support and said transverse lumbar support for enabling angular movement between said head support and said transverse lumbar support.

9. A method of exercising a lordotic arc in both the cervical and lumbar regions of a spine and promoting fluid imbibition through the cervical and lumbar regions comprising the steps of:

providing a head support including means for fastening said head support to a user's head;

providing a neck support on said head support;

providing a lumbar support;

securing said head support to a user's head such that the neck support is positioned transversely across a user's neck;

gradually inflating a first inflatable bladder between said neck support and said user's neck, causing said first inflatable bladder to expand in a first direction outwardly from said neck support and in a second direction transverse to the first direction, in order to impart a lordotic arc into the cervical regions of the spine and in order to traction the region on both sides of the lordotic arc, the expansion in the first direction being a distance greater than the expansion in the second direction;

alternately inflating and deflating the first bladder, while the user's head is secured to the support frame, in order to exercise the lordotic arc, exercise the cervical region and promote fluid imbibition therethrough;

gradually inflating a second inflatable bladder between said lumbar support and a user's lumbar spine, in order to impart a lordotic arc into the lumbar region of the spine and in order to traction the region on both sides of the lordotic arc; and alternately inflating and deflating the second bladder in order to exercise the lordotic arc, exercise the lumbar region, and promote fluid imbibition therethrough.

10. The method of claim 9 wherein the steps of alternately inflating and deflating the first and second bladders include inflating the bladders using a pump, and deflating the bladders using a release valve.

11. A method for imparting a forward curve to both the cervical and lumbar spine and manipulating the spine and intervertebral discs to promote fluid transfer to the discs, said method comprising the steps of:

providing a support frame;

providing a neck support caused by said frame;

providing a lumbar support caused by said frame;

positioning said neck support transversely across a back of a user's neck;

adjusting a distance between said neck support and said lumbar support and positioning said lumbar support transversely across a lumbar region of a user's spine;

inflating a bladder between the user's neck and the neck support, in a first expansion direction outwardly from said neck support toward the user's neck, forcing the cervical spine to curve forwardly, and in a second expansion direction normal thereto, thereby applying an angular traction to the cervical spine, said first expansion direction being a distance greater the second expansion direction;

inflating a bladder between the user's lumbar region and the lumbar support in a first direction outwardly from said lumbar support toward the user's lumbar region forcing the lumbar spine to curve forwardly, and in a second direction normal thereto, thereby applying an angular traction to the lumbar spine; and selectively inflating and deflating the bladders, forcing the cervical, cervico-thoracic, thoraco-lumbar and lumbar spine to curve forwardly and repeating inflation and deflation of the bladders in order to transfer fluid to the intervertebral discs.

12. The method according to claim 11 further including the step of securing the neck support to the head of the user prior to the step of inflating the bladder between the user's neck and the neck support.

* * * * *